United States Patent
Qian et al.

(10) Patent No.: US 10,149,041 B2
(45) Date of Patent: Dec. 4, 2018

(54) EARBUDS WITH COMPLIANT MEMBER

(71) Applicant: Apple Inc., Cupertino, CA (US)

(72) Inventors: Phillip Qian, San Jose, CA (US);
Edward Siahaan, San Francisco, CA (US); Erik L. Wang, Redwood City, CA (US); Christopher J. Stringer, Woodside, CA (US); Matthew Dean Rohrbach, San Francisco, CA (US); Daniel Max Strongwater, San Francisco, CA (US); Jason J. LeBlanc, Castro Valley, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 15/796,639

(22) Filed: Oct. 27, 2017

(65) Prior Publication Data

US 2018/0063621 A1   Mar. 1, 2018

Related U.S. Application Data

(63) Continuation of application No. 14/856,344, filed on Sep. 16, 2015, now Pat. No. 9,838,775.

(51) Int. Cl.
*H04R 1/10* (2006.01)
*A61B 5/024* (2006.01)
(Continued)

(52) U.S. Cl.
CPC ....... *H04R 1/1091* (2013.01); *A61B 5/02416* (2013.01); *A61B 5/6817* (2013.01);
(Continued)

(58) Field of Classification Search
CPC ...................................................... H04R 1/105
(Continued)

(56) References Cited

U.S. PATENT DOCUMENTS

| 5,715,321 A | 2/1998 | Andrea et al. |
| 8,121,325 B2 * | 2/2012 | Atamaniuk ............. H04M 1/05 381/322 |

(Continued)

FOREIGN PATENT DOCUMENTS

| CN | 101411072 | 4/2009 |
| KR | 1020100001360 | 6/2010 |

(Continued)

OTHER PUBLICATIONS

Taiwanese patent application No. TW105127789 , "Office Action", dated Jan. 15, 2018, 8 pages.
(Continued)

*Primary Examiner* — Gerald Gauthier
(74) *Attorney, Agent, or Firm* — Kilpatrick Townsend & Stockton LLP

(57) ABSTRACT

This application relates to earbuds configured with one or more biometric sensors. At least one of the biometric sensors is configured to be pressed up against a portion of the tragus for making biometric measurements. In some embodiments, the housing of the earbud can be symmetric so that the earbud can be worn interchangeably in either a left or a right ear of a user. In such an embodiment, the earbud can include a sensor and circuitry configured to determine and alter operation of the earbud in accordance to which ear the earbud is determined to be sitting in.

20 Claims, 15 Drawing Sheets

(51) Int. Cl.
  *A61B 5/00* (2006.01)
  *H04R 5/04* (2006.01)
  *H04R 1/40* (2006.01)
  *A61B 5/01* (2006.01)
  *A61B 5/1455* (2006.01)
  *H04R 5/033* (2006.01)
  *H04R 3/00* (2006.01)

(52) U.S. Cl.
  CPC ............ *H04R 1/105* (2013.01); *H04R 1/1016* (2013.01); *H04R 1/1041* (2013.01); *H04R 1/406* (2013.01); *H04R 5/04* (2013.01); *A61B 5/01* (2013.01); *A61B 5/14552* (2013.01); *A61B 5/14557* (2013.01); *H04R 1/1083* (2013.01); *H04R 3/005* (2013.01); *H04R 5/033* (2013.01); *H04R 2201/109* (2013.01); *H04R 2420/03* (2013.01); *H04R 2420/07* (2013.01); *H04R 2460/03* (2013.01)

(58) Field of Classification Search
  USPC .......... 381/58, 74, 309, 322, 328, 380, 381; 600/301; 715/716
  See application file for complete search history.

(56) References Cited

U.S. PATENT DOCUMENTS

| | | | |
|---|---|---|---|
| 8,600,096 B2 | 12/2013 | Lin et al. | |
| 8,611,578 B2 | 12/2013 | Kim et al. | |
| 8,655,004 B2 | 2/2014 | Hoellwarth et al. | |
| 8,774,435 B2* | 7/2014 | Ambrose | H04R 1/1091 381/328 |
| 8,873,786 B2 | 10/2014 | Olsen et al. | |
| 8,879,722 B1 | 11/2014 | Asrani et al. | |
| 9,161,114 B2 | 10/2015 | Murrells et al. | |
| 9,344,792 B2 | 5/2016 | Rundle | |
| 9,398,364 B2 | 7/2016 | Annunziato et al. | |
| 9,438,300 B1 | 9/2016 | Oliaei et al. | |
| 9,716,937 B2 | 7/2017 | Qian et al. | |
| 2006/0093131 A1 | 5/2006 | Cooper et al. | |
| 2007/0036363 A1 | 2/2007 | Hollemans et al. | |
| 2007/0049361 A1 | 3/2007 | Coote et al. | |
| 2007/0127757 A2 | 6/2007 | Darbut et al. | |
| 2008/0107301 A1 | 5/2008 | Kim et al. | |
| 2008/0152183 A1 | 6/2008 | Janik et al. | |
| 2008/0220831 A1 | 9/2008 | Alameh et al. | |
| 2008/0226114 A1* | 9/2008 | Thompson | H04R 1/1016 381/380 |
| 2008/0310666 A1* | 12/2008 | Wengreen | H04R 1/026 381/381 |
| 2009/0010461 A1 | 1/2009 | Klinghult et al. | |
| 2009/0097689 A1* | 4/2009 | Prest | H04R 1/028 381/380 |
| 2009/0116666 A1 | 5/2009 | Ranta et al. | |
| 2009/0131124 A1 | 5/2009 | Bibaud et al. | |
| 2009/0154739 A1 | 6/2009 | Zellner et al. | |
| 2010/0020998 A1 | 1/2010 | Brown et al. | |
| 2010/0114188 A1 | 5/2010 | Chan et al. | |
| 2010/0217098 A1* | 8/2010 | LeBoeuf | A61B 5/00 600/301 |
| 2010/0217102 A1 | 8/2010 | LeBoeuf et al. | |
| 2011/0007929 A1* | 1/2011 | Rabu | H04R 1/1033 381/380 |
| 2011/0066941 A1* | 3/2011 | Chipchase | G06F 3/167 715/716 |
| 2011/0129097 A1 | 6/2011 | Andrea et al. | |
| 2011/0206215 A1 | 8/2011 | Bunk et al. | |
| 2012/0114132 A1* | 5/2012 | Abrahamsson | H04R 1/1016 381/74 |
| 2012/0114154 A1 | 5/2012 | Abrahamsson et al. | |
| 2012/0207317 A1 | 8/2012 | Abdollahzadeh Milani et al. | |
| 2012/0224731 A1 | 9/2012 | Zellner et al. | |
| 2013/0028446 A1 | 1/2013 | Krzyzanowski et al. | |
| 2013/0083933 A1 | 4/2013 | Aase et al. | |
| 2013/0121494 A1 | 5/2013 | Johnston | |
| 2013/0131519 A1 | 5/2013 | LeBoeuf et al. | |
| 2013/0177193 A1* | 7/2013 | Orzel | H04R 1/1033 381/380 |
| 2013/0236027 A1 | 9/2013 | Tao et al. | |
| 2013/0279724 A1 | 10/2013 | Stafford et al. | |
| 2013/0336495 A1* | 12/2013 | Burgett | H04R 1/1091 381/74 |
| 2014/0016803 A1* | 1/2014 | Puskarich | H04R 1/1041 381/309 |
| 2014/0093091 A1 | 4/2014 | Dusan et al. | |
| 2014/0093093 A1 | 4/2014 | Dusan et al. | |
| 2014/0146982 A1 | 5/2014 | Pelosi et al. | |
| 2014/0270231 A1 | 9/2014 | Dusan et al. | |
| 2014/0288447 A1 | 9/2014 | Luna et al. | |
| 2015/0023516 A1 | 1/2015 | Rabii et al. | |
| 2015/0181337 A1 | 6/2015 | Rodgers | |
| 2015/0195639 A1 | 7/2015 | Azmi et al. | |
| 2015/0201271 A1 | 7/2015 | Diethorn et al. | |
| 2015/0245129 A1 | 8/2015 | Dusan et al. | |
| 2015/0310846 A1 | 10/2015 | Goldstein et al. | |
| 2015/0325251 A1 | 11/2015 | Dusan et al. | |
| 2015/0382100 A1 | 12/2015 | Azmi et al. | |
| 2016/0094899 A1 | 3/2016 | Aumer et al. | |
| 2016/0192039 A1 | 6/2016 | Negi et al. | |
| 2016/0205457 A1* | 7/2016 | Whitney | H04R 1/1033 381/380 |
| 2016/0205475 A1 | 7/2016 | Shanmugam et al. | |
| 2016/0217780 A1 | 7/2016 | Cagdaser et al. | |
| 2016/0249141 A1 | 8/2016 | Verdooner et al. | |
| 2016/0261147 A1 | 9/2016 | Blum et al. | |
| 2016/0294225 A1 | 10/2016 | Blum et al. | |
| 2016/0316285 A1 | 10/2016 | Qian et al. | |
| 2016/0361020 A1 | 12/2016 | Romesburg et al. | |
| 2016/0381448 A1 | 12/2016 | Qian et al. | |
| 2017/0064427 A1 | 3/2017 | Rich et al. | |
| 2017/0078780 A1 | 3/2017 | Qian et al. | |
| 2017/0078781 A1 | 3/2017 | Qian et al. | |
| 2017/0078785 A1 | 3/2017 | Qian et al. | |
| 2018/0063621 A1* | 3/2018 | Qian | H04R 1/406 |

FOREIGN PATENT DOCUMENTS

| | | |
|---|---|---|
| TW | 201220861 | 5/2012 |
| TW | M497005 | 3/2015 |
| WO | 2014116924 | 7/2014 |

OTHER PUBLICATIONS

105127789 , "Office Action", dated Sep. 13, 2017.
U.S. Appl. No. 14/856,298 , "First Action Interview Pilot Program Pre-Interview Communication", dated Nov. 23, 2016, 4 pages.
U.S. Appl. No. 14/856,298 , "Notice of Allowance", dated Feb. 27, 2017, 11 pages.
U.S. Appl. No. 14/856,298 , "Restriction Requirement", dated Jul. 20, 2016, 5 pages.
U.S. Appl. No. 14/856,298 , "Supplemental Notice of Allowance", dated Apr. 3, 2017, 2 pages.
U.S. Appl. No. 14/856,344 , "First Action Interview Pilot Program Pre-Interview Communication", dated Nov. 9, 2016, 5 pages.
U.S. Appl. No. 14/856,344 , "Non-Final Office Action", dated Mar. 24, 2017, 10 pages.
U.S. Appl. No. 14/856,344 , "Notice of Allowance", dated Jan. 13, 2017, 10 pages.
U.S. Appl. No. 14/856,344 , "Notice of Allowance", dated Jul. 27, 2017, 9 pages.
U.S. Appl. No. 14/856,402 , "Non-Final Office Action", dated Nov. 4, 2016, 17 pages.
U.S. Appl. No. 14/856,402 , "Notice of Allowance", dated Mar. 14, 2017, 12 pages.
PCT/US2016/048674 , "International Search Report and Written Opinion", dated Oct. 12, 2016, 12 pages.

(56) References Cited

OTHER PUBLICATIONS

TW105127789 , "Office Action", dated Sep. 13, 2017, 10 pages.

\* cited by examiner

EARBUDS WITH COMPLIANT MEMBER

CROSS-REFERENCES TO RELATED APPLICATIONS

This application is a continuation of U.S. patent application Ser. No. 14/856,344, filed on Sep. 16, 2015. This application is related to the following U.S. patent applications: Ser. No. 14/856,298, filed Sep. 16, 2015, entitled "Earbuds with Biometric Sensing;" Ser. No. 14/856,402, filed Sep. 16, 2015, entitled "Earbuds with Biometric Sensing,". Each of these references is hereby incorporated by reference in their entirety for all purposes.

FIELD

The described embodiments relate generally to the integration of biometric sensors into an earbud. More particularly, the present embodiments are directed towards positioning a biometric sensor along an exterior surface of the earbud so it can be placed in direct contact with a portion of a user's ear during use of the earbud.

BACKGROUND

Portable electronic device users have shown increasing interest in biometric tracking. Biometric sensors often need to be in close or even direct contact with the skin to properly measure and track biometric parameters along the lines of heart rate, $VO_2$, and core temperature. Requiring a user to place a sensor in direct contact with the skin to track these types of biometric data can be overly burdensome, making adoption of the biometric tracking more difficult. Consequently, mechanisms for unobtrusively measuring biometric parameters are highly desirable.

SUMMARY

This disclosure describes various embodiments that relate to ways in which biometric sensors can be configured for optimal use with an audio accessory device.

An earbud is disclosed that includes at least the following elements: a housing defining an opening proximate a first end of the housing; a speaker disposed within the housing and oriented so that audio emitted by the speaker exits the housing through the opening defined by the housing; a biometric sensor positioned along an exterior surface of the housing at the first end of the housing; and a compliant member coupled with a second end of the housing.

An audio device is disclosed that includes at least the following elements: a first earbud and a second earbud, each earbud including: an earbud housing, a speaker disposed within the earbud housing and configured to project audio out of an opening defined by the earbud housing, circuitry configured to receive audio data and transmit the audio data to the speaker, and a compliant member coupled with the earbud housing.

An earbud is disclosed that includes at least the following: an earbud housing; a speaker disposed within the earbud housing; and a compliant member including a first end pivotally coupled to a first portion of the earbud housing and a second end pivotally coupled to a second portion of the earbud housing, the compliant member configured to deform to conform with an interior geometry of an ear of a user and to exert a force on the earbud housing that seats the earbud housing proximate the ear canal of the ear of the user when being worn by the user. The compliant member can take the form of an elastomeric loop. In some embodiments, the compliant member can be at least partially reinforced by an amount of flexible metal. The pivotal coupling between the compliant member and the earbud housing can take the form of a hinge with end stops. In some embodiments, the end stops can include contacts that help determine a rotational position of each end of the compliant member with respect to the earbud housing.

An audio device is disclosed that includes at least the following elements: a device housing having a size and shape suitable for at least partial insertion into an ear of a user; a speaker disposed within the device housing; a biometric sensor disposed within the device housing and including a sensing surface arranged along an exterior surface of the device housing; and a processor configured to determine an orientation of the device housing within the ear of a user using a value of a biometric parameter detected by the biometric sensor and adjust an operational state of the speaker in accordance with the determined orientation A method for controlling operation of an earbud is disclosed. The method includes receiving a signal from an orientation sensor of the earbud consistent with the earbud being worn in a first ear of a user; sending only a first audio channel of a multi-channel audio signal to a speaker unit of the earbud, the first audio channel being associated with the first ear of the user; and adjusting an operational state of a sensor of the earbud in accordance with the signal received from the orientation sensor.

An audio device is disclosed that includes at least the following elements: a speaker; a wireless transceiver; a biometric sensor for measuring a biometric parameter of a user of the audio device; an energy storage device providing power for operation of the speaker, the biometric sensor and the wireless transceiver; and an earbud housing enclosing the speaker, the wireless transceiver the biometric sensor and the energy storage device. The biometric parameter measured by the biometric sensor is utilized to determine an orientation of the earbud housing within an ear of a user of the audio device, the determination of the orientation then utilized to change an operating characteristic of the speaker.

An earbud is disclosed that includes at least the following elements: an orientation sensor configured to determine an orientation of the earbud within an ear of a user of the earbud; a microphone array including multiple microphones; and circuitry configured to adjust an operational state of the microphones of the microphone array in accordance with information provided by the orientation sensor.

An audio device is disclosed that includes at least the following elements: a device housing having a shape and size suitable for at least partial insertion into an ear of a user; an orientation sensor configured to provide an orientation of the device housing with respect to the ear of the user; an array of microphones disposed within the device housing, the array of microphones including a first microphone, a second microphone, and a third microphone; and a processor configured to adjust an operational state of the first and second microphones in accordance with the orientation of the device housing.

An audio device is disclosed that includes at least the following elements: a speaker; a wireless transceiver; a biometric sensor configured to measure both an orientation of the audio device in an ear of a user and a biometric parameter; a microphone array; an energy storage device providing power for the audio device; and an earbud housing enclosing the speaker, the microphone array, the wireless transceiver, the biometric sensor and the energy storage device. The orientation of the earbud housing within the ear of the user of the audio device is utilized to adjust an operating state of the microphone array.

BRIEF DESCRIPTION OF THE DRAWINGS

The disclosure will be readily understood by the following detailed description in conjunction with the accompanying drawings, wherein like reference numerals designate like structural elements, and in which.

Figure 1:
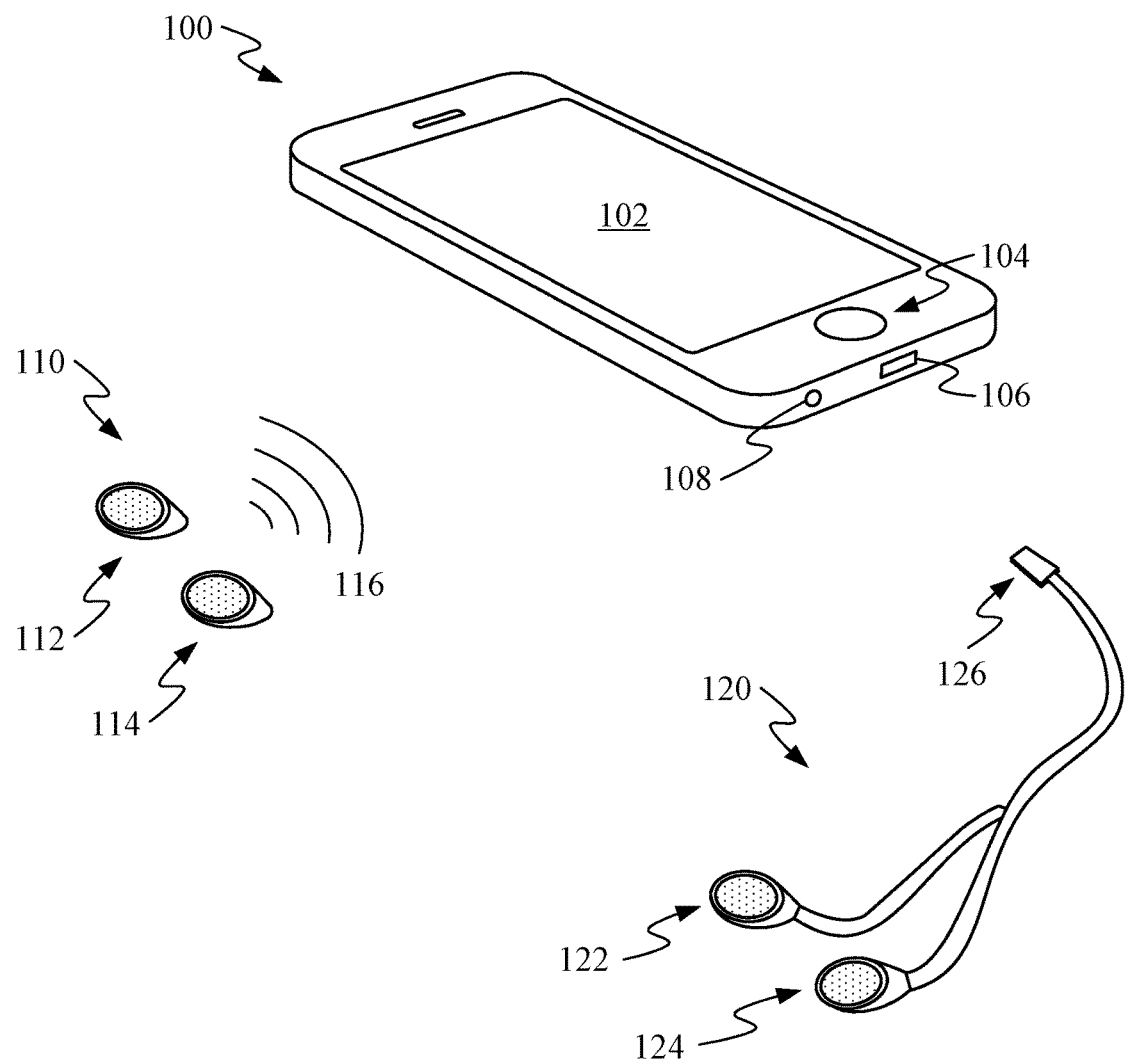
FIG. 1 shows an exemplary device suitable for use with the described embodiments.

Other aspects and advantages of the invention will become apparent from the following detailed description taken in conjunction with the accompanying drawings which illustrate, by way of example, the principles of the described embodiments.

DETAILED DESCRIPTION

Representative applications of methods and apparatus according to the present application are described in this section. These examples are being provided solely to add context and aid in the understanding of the described embodiments. It will thus be apparent to one skilled in the art that the described embodiments may be practiced without some or all of these specific details. In other instances, well known process steps have not been described in detail in order to avoid unnecessarily obscuring the described embodiments. Other applications are possible, such that the following examples should not be taken as limiting.

In the following detailed description, references are made to the accompanying drawings, which form a part of the description and in which are shown, by way of illustration, specific embodiments in accordance with the described embodiments. Although these embodiments are described in sufficient detail to enable one skilled in the art to practice the described embodiments, it is understood that these examples are not limiting; such that other embodiments may be used, and changes may be made without departing from the spirit and scope of the described embodiments.

Biometric sensors can take many forms and can be configured to measure a large range of biometric parameters. Unfortunately, persistent, long-term monitoring of these biometric parameters can be challenging and/or undesirable when the monitoring interferes with any aspect of a user's everyday life. One way to make the incorporation of biometric sensors into a user's everyday life more palatable is to integrate the sensors with a type of device that the user already utilizes. Alternatively, the biometric sensor or sensors can also be integrated into a wearable device that can be worn unobtrusively.

Wearable devices that can be configured with a biometric sensor include a set of earphones and an individual earbud. Because the earbud portion of the earphones sits at least partially within the ear canal of a user during use, an exterior surface of the earbud contacts various portions of the ear to keep it positioned within the ear of a user. One exemplary type of biometric sensor that can be used to record biometric parameters of a user is a photoplethysmogram (PPG) sensor that measures biometric parameters by shining light and then measuring the reflectivity of that light off the skin. Variations in the reflectivity can be used to characterize profusion of the blood through the skin of a user. Unfortunately, the exterior surface of a conventional earbud doesn't typically make sufficiently solid and/or consistent contact with a well-profused portion of the ear to provide reliable biometric parameter measurements. One solution to this problem is to arrange the PPG sensor along a surface of the earbud at an end of the earbud near a speaker opening of the earbud. In this way, when the speaker opening is aligned with the ear canal, the PPG sensor can contact an interior facing surface of the tragus of the ear. Contact between the interior facing surface of the tragus of the ear and the PPG sensor can be maintained by adding a compliant member to an opposing end of the earbud. The compliant member can then engage an opposite surface of the ear known as the concha so that the earbud is wedged between two opposing surfaces of the ear. By choosing a compliant member formed of compressible or otherwise deformable material, the earbud can be well-suited to fit within the ears of a broad spectrum of users.

An earbud can also be equipped with various other sensors that can work independently or in concert with the biometric sensor described above. For example, in some embodiments, the other sensors can take the form of an orientation sensor to help the earbud determine which ear the earbud is positioned within and then adjust operation of the earbud in accordance with that determination. In some embodiments, the orientation sensor can be a traditional inertial-based sensor while in other embodiments, sensor readings from another biometric sensor such as a proximity sensor or a temperature sensor can be used to make an orientation determination.

An earbud with the aforementioned sensors can also include additional sensors such as a microphone or array of microphones. In some embodiments, at least two microphones from a microphone array can be arranged along a line pointed towards or at least near the mouth of a user. By using information received by the orientation sensor or sensors, a controller within the earbud can determine which microphones of a microphone array should be activated to obtain this configuration. By activating only those microphones arranged along a vector pointed at or near the mouth, ambient audio signals not originating near the mouth can be ignored by applying a spatial filtering process.

These and other embodiments are discussed below with reference to FIGS. 1-12; however, those skilled in the art will readily appreciate that the detailed description given herein with respect to these figures is for explanatory purposes only and should not be construed as limiting.

FIG. 1 shows a portable media device 100 suitable for use with a variety of accessory devices. Portable media device 100 can include touch sensitive display 102 configured to provide a touch sensitive user interface for controlling portable media device 100 and in some embodiments any accessories to which portable media device 100 is electrically or wirelessly coupled. In some embodiments, portable media device 100 can include additional controls such as, for example, button 104. Portable media device 100 can also include multiple hard-wired input/output (I/O) ports that include digital I/O port 106 and analog I/O port 108. Accessory device 110 can take the form of an audio device that includes two separate earbuds 112 and 114. Each of earbuds 112 and 114 can include wireless receivers or transceivers capable of establishing a wireless link 116 with portable media device 100. Accessory device 120, which can also be compatible with portable media device 100, can take the form of a wired audio device that includes earbuds 122 and 124. Earbuds 122 and 124 can be electrically coupled to each other and to a connector plug 126 by a number of wires. In embodiments where connector plug 126 is an analog plug sensors within either one of earbuds 122 and 124 can receive power through analog I/O port 108 while transmitting data by way of a wireless protocol such as Bluetooth, Wi-Fi, or the like. In embodiments where connector plug 126 interacts with digital I/O port 106, sensor data and audio data can be freely passed through the wires during use of portable media device 100 and accessory device 120. It should be noted that earbuds 122 and 124 can be swappable between left and right ears when the wire attached to each earbud is attached along a line of symmetry of each earbud, or alternatively when the wire is attached by a pivoting coupling. Stereo channels can be swapped between wires when attached to digital I/O port 106.

Figure 2:
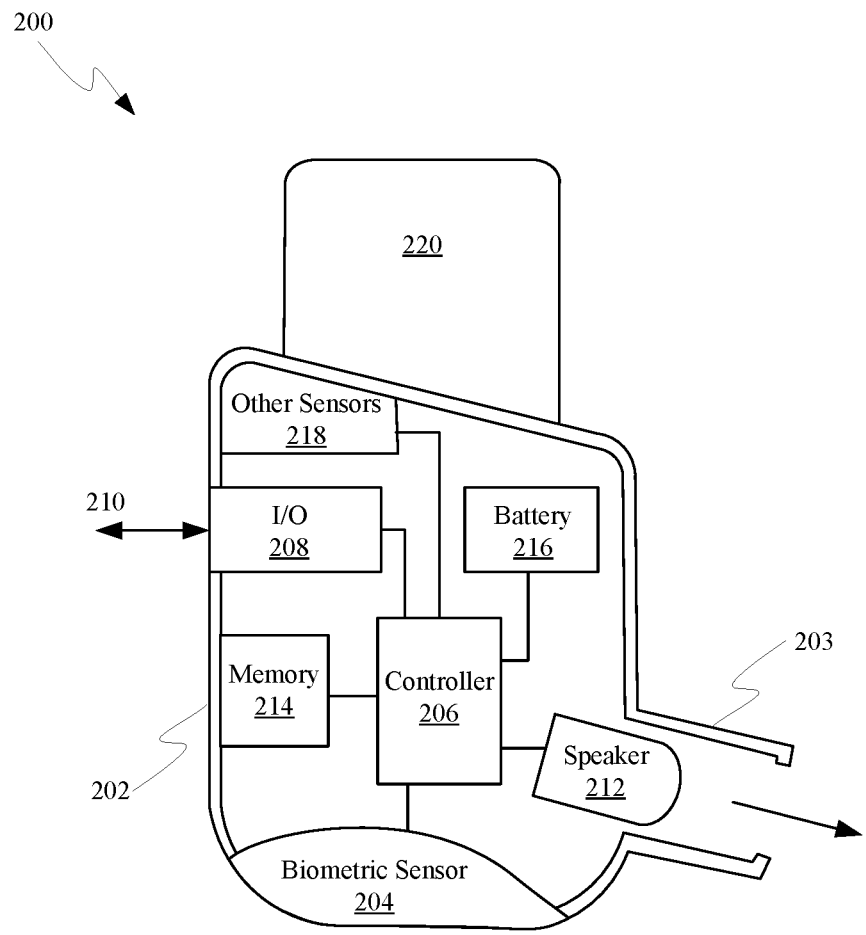
FIG. 2 shows a cross-sectional view of an earbud device that includes a number of electrical components used to support the described device functionality.

FIG. 2 shows a schematic view of an earbud 200 that can be incorporated into accessory device 110 as earbud 112 and/or earbud 114 or incorporated into accessory device 120 as earbud 122 and/or earbud 124. In some embodiments, earbud 200 can include a housing 202. Housing 202 can have a size and/or shape that allows it to be easily inserted within the ear of an end user. Housing 202 also defines an interior volume within which numerous electrical components can be distributed. In particular, a biometric sensor 204 can be situated within or at least supported by housing 202. As depicted, biometric sensor 204 can be arranged within and close an opening in housing 202. In this way, biometric sensor 204 can have an exterior facing sensing surface capable of interacting with and measuring external stimuli. Housing 202 can also include a protrusion 203 with an opening at a distal end of the protrusion 203 that provides a channel through which audio signals can be transmitted out and into the ear canal of a user of earbud 200, as indicated by the arrow.

In some embodiments, biometric sensor 204 can take the form of a photoplethysmogram (PPG) sensor. A PPG sensor utilizes a pulse oximeter to illuminate a patch of skin and measure changes in light absorption of the skin. The pulse oximeter can include one or more light emitting devices and one or more light collecting devices. In some embodiments, the light emitting device can take the form of a light emitting diode (LED) and the light collecting device can take the form of a photodiode for measuring the changes in light absorption. The changes in light absorption can be caused by the profusion of blood within the skin during each cardiac cycle. Because the profusion of blood into the skin can be affected by multiple other physiological systems this type of biometric monitoring system can provide many types of biometric information. By capturing wave forms associated with the cycling profusion of blood to the skin, multiple biometric parameters can be collected including, for example, heart rate, blood volume and respiratory rate. By using LEDs that emit different wavelengths of light additional data can be gathered such as, for example, $VO_2$ max (i.e., the maximal rate of oxygen absorption by the body). By arranging biometric sensor 204 in the depicted position with respect to housing 202, biometric sensor 204 can be placed in contact with a tragus of the ear, which advantageously tends to get well-profused with blood, thereby allowing sensor readings made by a pulse oximeter in the area of the tragus to be particularly accurate. In some embodiments, biometric sensor 204 can take the form of a core temperature sensor. Other embodiments of biometric sensor 204 include embodiment in which the biometric sensor takes the form of an electrode. When the earbud is a wired earbud electrically coupled to another earbud with an electrode, the electrodes can cooperatively measure a number of different biometric parameters. In some embodiments, the electrodes can be configured to measure the galvanic skin response (GSR) of a user. A GSR can be useful in determining an amount of stress being experienced by the user at any given moment in time. In some embodiments, the electrodes can be used to measure more detailed parameters of the heart by taking the form of an electrocardiogram (EKG) sensor or an impedance cardiography (ICG) sensor.

Biometric sensor 204 can be in electrical communication with at least controller 206, which is responsible for controlling various aspects of earbud 200. For example, controller 206 can gather biometric sensor data recorded by biometric sensor 204 and pass that data along to input/ouput (I/O) interface 208. I/O interface 208 can be configured to transmit the biometric sensor data to another device such as, for example, portable media device 100 by way of link 210. Link 210 can be generated in various ways. For example, link 210 can be a wireless link when I/O interface 208 takes the form of a wireless transceiver suitable for use in an accessory such as accessory device 110 depicted in FIG. 1. Alternatively, link 210 can be transmitted over a wired connector such as the wires depicted with accessory device 120. In addition to providing a conduit for transmitting biometric sensor data provided by biometric sensor 204, I/O interface 208 can also be used to receive audio content that can be processed by controller 206 and sent on to speaker 212. I/O interface 208 can also receive control signals from a device similar to portable media device 100 for accomplishing tasks such as adjusting a volume output of speaker 212 or modifying a sensitivity, priority or duty cycle of biometric sensor 204. When I/O interface 208 takes the form of a wireless transceiver, I/O interface 208 can include an antenna configured to transmit and receive signals through an antenna window or an opening defined by housing 202. This can be particularly important when housing 202 is formed of radio opaque material. In some embodiments, I/O interface 208 can also represent one or more exterior controls (e.g. buttons and/or switches) for performing tasks such as pairing earbud 200 with another device or adjusting various settings of earbud 200 such as volume or the like.

Earbud 200 can also include memory 214, which can be configured to carry out any number of tasks. For example, memory 214 can be configured to store media content when a user of earbud 200 wants to use earbud 200 independent from any other device. In such a use case, memory 214 can be loaded with one or more media files for independent playback. When earbud 200 is being used with another device, memory 214 can also be used to buffer media data received from the other device. In the independent use case described above, memory 214 can also be used to store sensor data recorded by biometric sensor 204. The sensor data can then be sent to a device along the lines of portable media device 100 once the two devices are in communication.

With the possible exception of when I/O interface 208 is a wired interface that can provide power to earbud 200 from another device or power source, battery 216 is generally used for powering operations of earbud 200. Battery 216 can provide the energy needed to perform any of a number of tasks including: maintain a wireless link 210, powering controller 206, driving speaker 212, powering biometric sensor 204 and powering any other sensors 218. While other sensors are shown as a generic block, other sensors 218 can include sensors such as microphones, orientation sensors, proximity sensors or any other sensor suitable for improving the user experience of earbud 200. In some embodiments, one or more of sensors 218 can be used in combination with biometric sensor 204 to improve accuracy or calibrate various results. It should be noted that other sensors 218 are not required in all of the embodiments described herein.

Earbud 200 can also include a compliant member 220 coupled with an exterior surface of housing 202. Compliant member 220 can be configured to provide an interference fit for earbud 200 within the ear of a user. As there can be large variations in the size and shape of the ears of any particular user, the compliant member allows earbud 200 to conform to a number of different ear shapes and sizes. Furthermore, in some configurations compliant member 220 can be removable so that various different compliant member sizes and shapes can be used to further customize the overall size of earbud 200 to the ear of any user. Compliant member 220 can be made from any of a number of different types of materials including, for example, open-cell foam, thermoplastic elastomers (TPE) and the like. In some embodiments, a material used to construct compliant member 220 can be configured to provide more force upon the ear of a user resulting in a more robust fit within the ear of a user. A compliant member constructed in this way can be better suited for athletic activities.

Figure 3A:
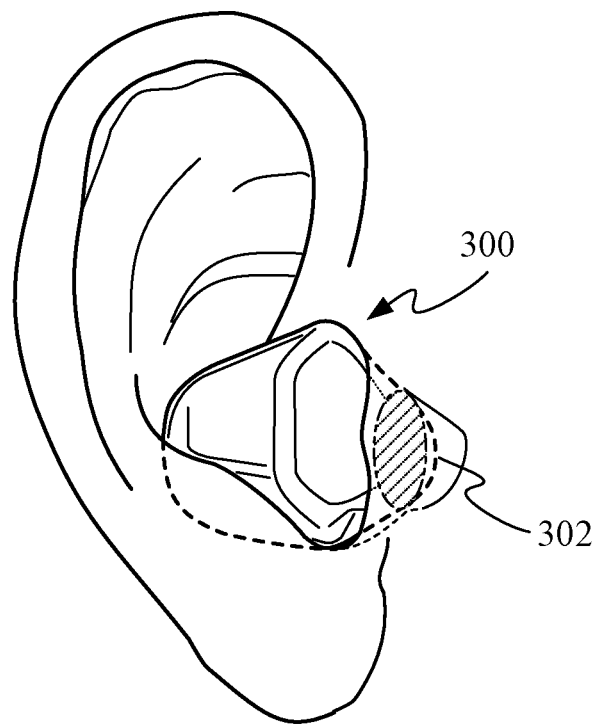
FIGS. 3A-3B show views of an earbud situated in the ear of a user and how a biometric sensor of the earbud contacts the tragus of the user.
Figure 3B:
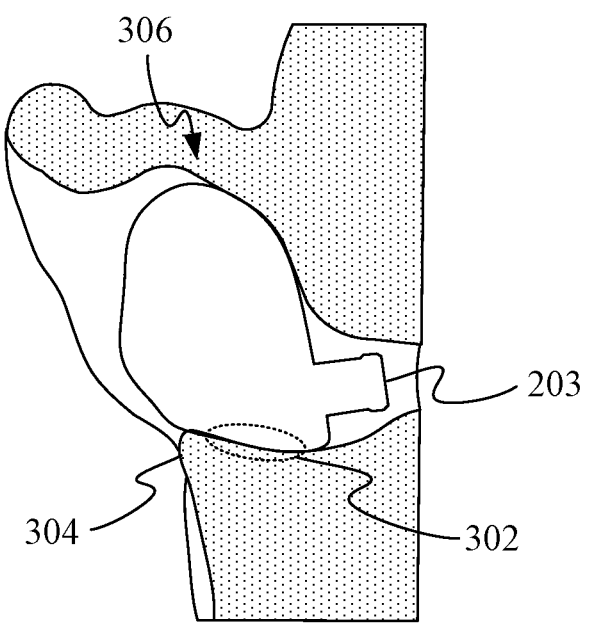

FIGS. 3A-3B show views of housing 202 positioned within an ear of a user. FIG. 3A depicts interference region 302, which represents an interface area between biometric sensor 204 and the tragus 304 of the user. FIG. 3B depicts how protrusion 203 can be positioned within the ear canal of the user to minimize an amount of power lost as audio content exits housing 202. While FIGS. 3A-3B don't specifically point out compliant member 220, it should be understood that housing 202 can include a rear compliant portion integrated within housing 202 that can accommodate a certain amount of compression that allows secure seating of housing 202 within the ear of the user. As depicted in FIG. 3B housing 202 of earbud 300 is compressed between tragus 304 and concha 306 of the depicted ear, thereby preventing earbud 300 from being dislodged from the ear and maintaining a consistent amount of pressure sufficient to keep biometric sensor 204 consistently engaged in interference region 302.

Figure 4A:
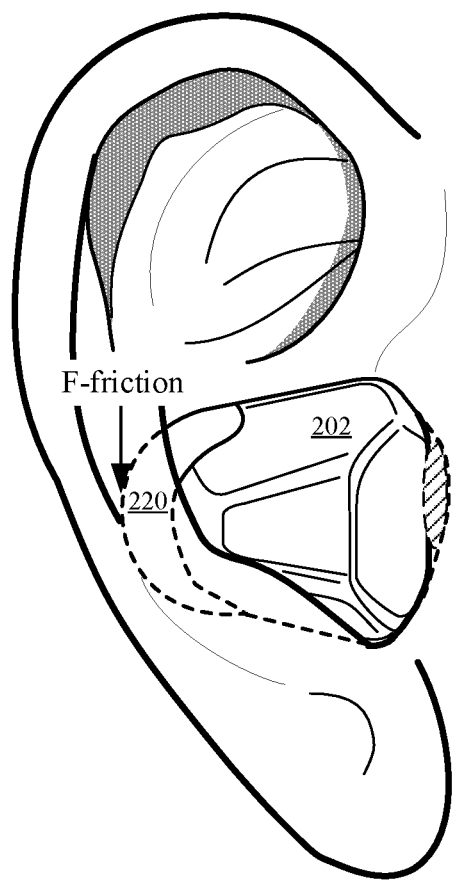
FIGS. 4A-4B show a number of views of an earbud having a biasing member taking the form of a compliant member.
Figure 4B:
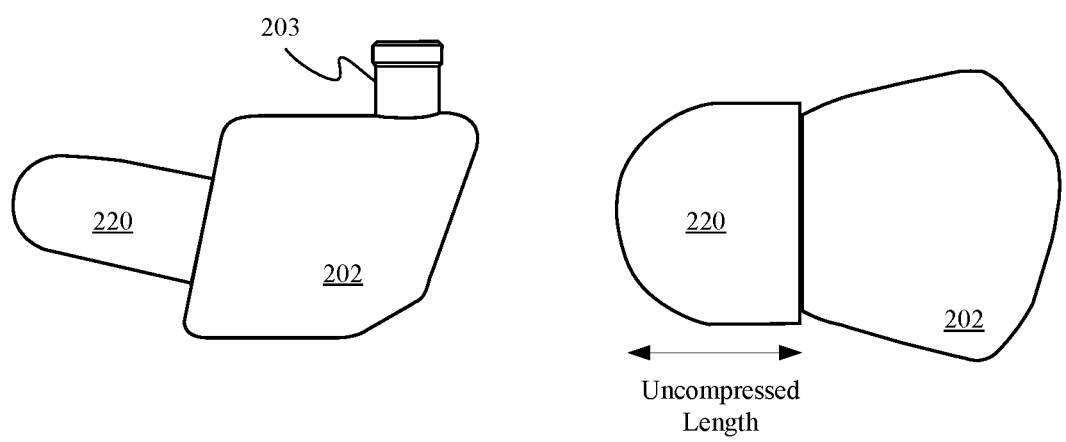

FIGS. 4A-4B show views of housing 202 and compliant member 220 of earbud 200 situated within the ear of a user. In particular, frictional forces acting upon compliant member 220 are depicted in FIG. 4A. The depicted forces show how compressive and friction forces generated between compliant member 220 and the concha of the ear can help maintain earbud 200 within the ear of the user. FIG. 4A also shows a slight variation of the compliant member design depicted in FIG. 2 in that compliant member 220 is situated within a channel defined by housing 202. In this way, housing 202 can be made substantially larger while still allowing compliant member 220 to deform within the channel to yield a satisfactory fit and feel for the user of earbud 200. FIG. 4B shows top and side views of earbud 200. In particular an uncompressed length dimension of compliant member 220 can be about 9 mm. It should be noted that this length is given for exemplary purposes only and that varying lengths are possible and even desirable to accommodate various ear geometries of different users.

Figure 4C:
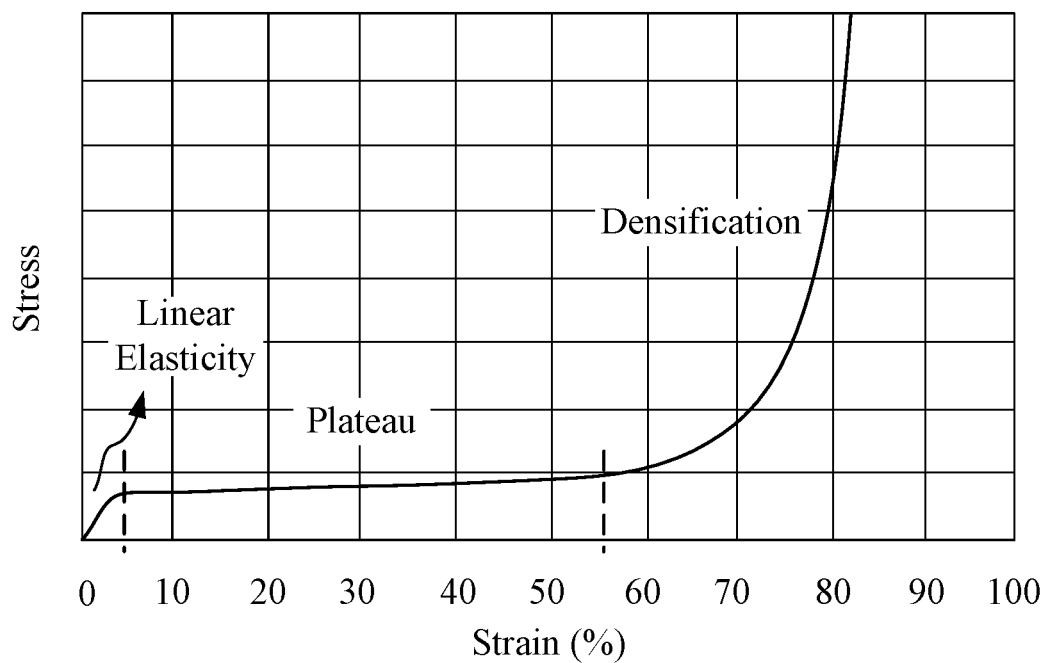
FIG. 4C shows how the compliant member depicted in FIGS. 4A-4B can be configured to provide a fixed amount of force for users having a varied ear sizes.

FIG. 4C depicts a graph showing stress with respect to strain for an exemplary compliant member 220. By making a careful material choice, FIG. 4C shows how an amount of stress provided by compliant member 220 can be kept substantially the same over a large range of strain. For example, a user with a smaller ear size that causes a change in length of about 50% would only experience a slightly greater amount of stress than a user with larger ears who only ends up compressing compliant member 220 by about 20%. In this way, a compliant member of a particular size can accommodate ears having a wide range of sizes, while substantially maintaining an amount of force placed on the ear of a user. In this way, situations in which the compliant member 220 exerts a painful amount of force or conversely not enough force to maintain earbud 200 within the ear can be avoided.

Figure 5A:
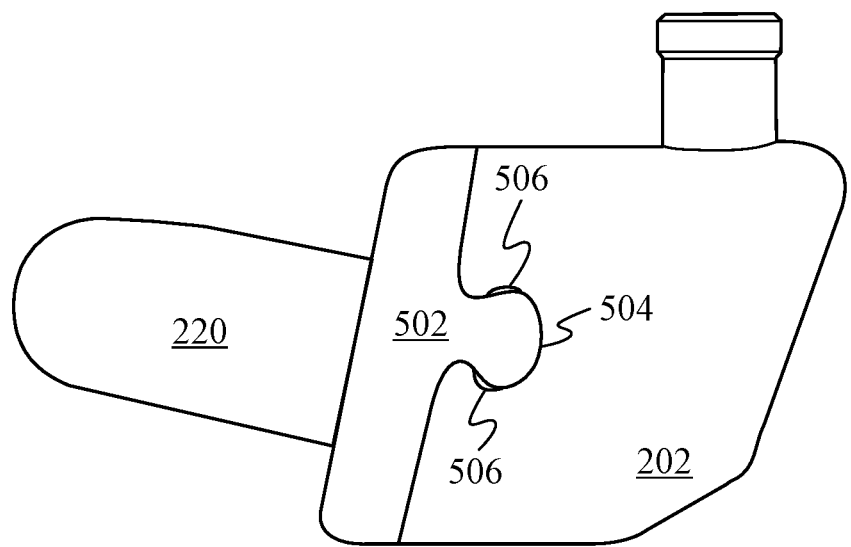
FIGS. 5A-5B shows how the biasing member can be interchangeably removed from an earbud by way of a locking channel.
Figure 5B:
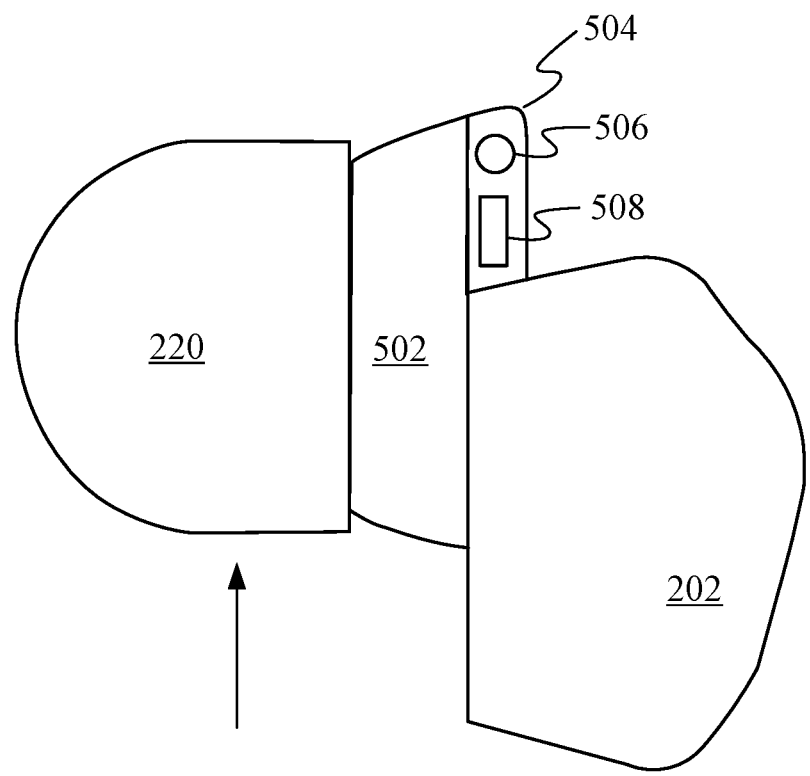

FIGS. 5A-5B show an embodiment in which a compliant member 220 can be conveniently removed from housing 202. In this embodiment, FIG. 5A shows linking feature 502 affixed to compliant member 220. In some embodiments, linking feature 502 can act solely as a convenient mechanism for swapping out compliant member 220 with larger compliant members, smaller compliant members or compliant members formed of different materials. Linking feature 502 also acts as an extension of housing 202 as depicted. In some embodiments, linking feature 502 can include add-on modules along the lines of additional memory storage for custom media or software content, additional biometric or orientation sensors, and/or additional battery cells. For example, the custom software content can include a mobile application for use with a device similar to portable media device 100. When linking feature 502 includes additional sensors, the sensor within linking feature 502 can provide additional functionality for the earbud. For example, the sensor within linking feature 502 can take the form of a temperature sensor, a capacitive sensor, a microphone or an electrode. Once linking feature 502 is coupled with housing 202 then any sensor within linking feature 502 can begin providing sensor data and/or gather sensor data cooperatively with the sensor disposed within housing 202.

Linking feature 502 also includes a puzzle shaped protrusion 504 engaged within a channel defined by housing 202. Protrusion 504 can include locking features 506, which can take the form of spring loaded ball bearings that helps to secure linking feature 502 with housing 202 once linking feature 502 is properly aligned with housing 202. In some embodiments, protrusion 504 can include environmental seals at each end that prevent the intrusion of sweat or moisture between the interface of protrusion 504 and the channel defined by housing 202.

FIG. 5B shows how protrusion 504 can also include one or more electrical contacts 508. Electrical contacts 508 can match up with electrical contacts positioned within the channel defined by housing 202. In this way, when contacts 508 and the contacts of housing 202 are aligned a robust electrical connection between components disposed within linking feature 502 and housing 202 is formed. This robust electrical connection can be used to facilitate the sensor communication briefly discussed above and/or provide memory with housing 202 access to memory onboard linking feature 502. When the communication between linking feature 502 and housing 202 is initially formed linking feature 502 can provide identification to a controller disposed within housing 202 so that the controller understands the additional functionality added by linking feature 502. In some embodiments, the identification can be communicated to the user in various ways. For example, the user can be apprised of the new functionality by audio signals broadcast by the earbud or even by sending a message to a media player along the lines of portable media player 100.

Figure 6A:
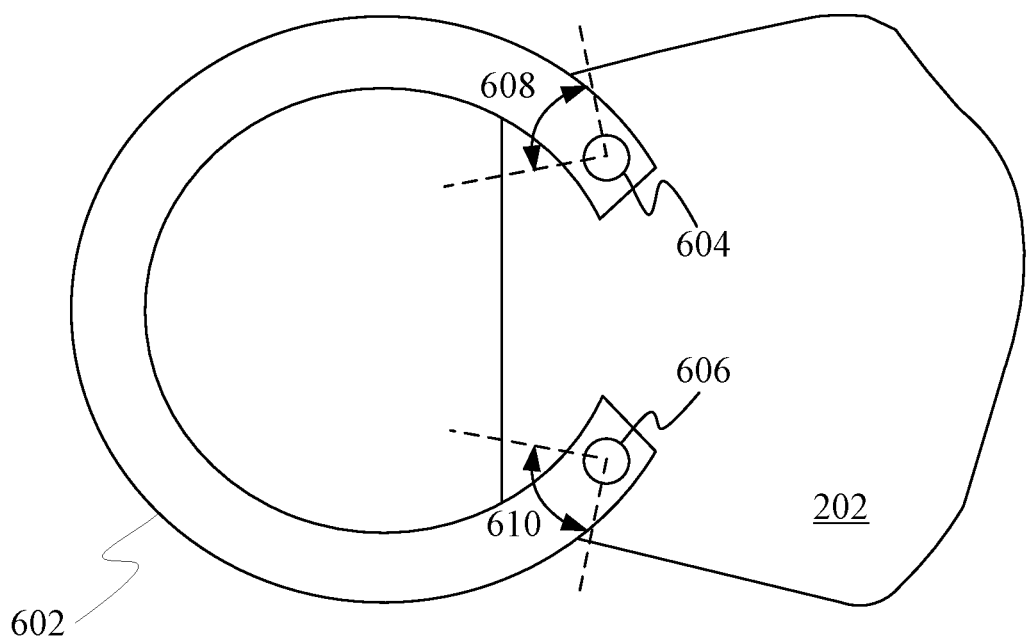
FIGS. 6A-6C show side views of an earbud having a biasing member taking the form of a deformable loop pivotally coupled with the earbud.

FIG. 6A shows a side view of an alternative embodiment in which a compliant member 602 takes the form of a loop of flexible material, each of its two ends being pivotally coupled to housing 202 at two different positions. The pivotal coupling can be accomplished by hinges 604 and 606. Hinges 604 and 606 can be configured to provide ranges of motion 608 and 610 respectively. In some embodiments, range of motion 608 can be the same as range of motion 610, while in other embodiments the ranges can be either slightly or substantially different. Hinges 604 and 606 allow compliant member 602 to have a substantial range of motion, which can assist compliant member 602 in fitting a wide range of ear shapes and geometries. In some embodiments, end stops associated with each of hinges 604 and 606 can take the form of electrical contacts that communicate positional information to a controller of earbud 200. In such a configuration, earbud 200 can be configured to alter its playback in accordance with information provided by the electrical contacts.

Figure 6B:
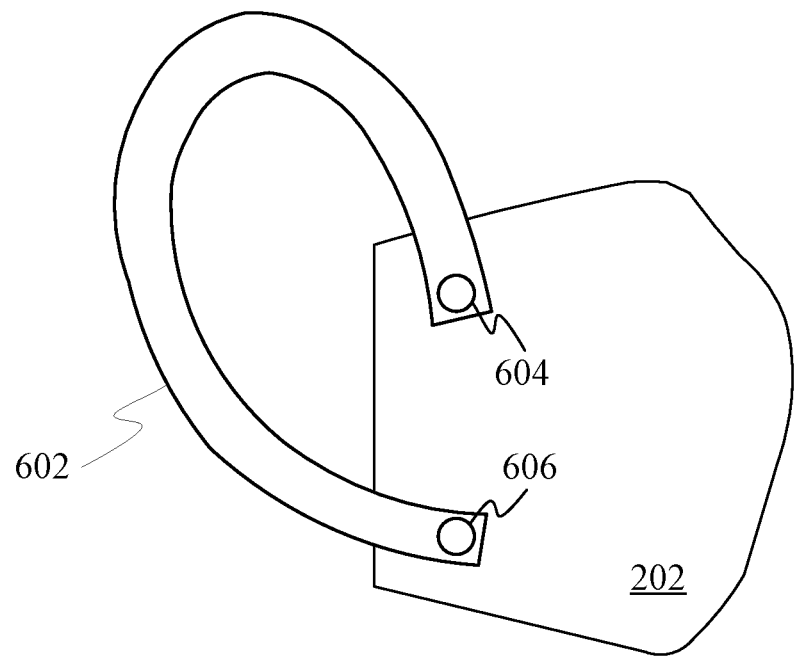
Figure 6C:
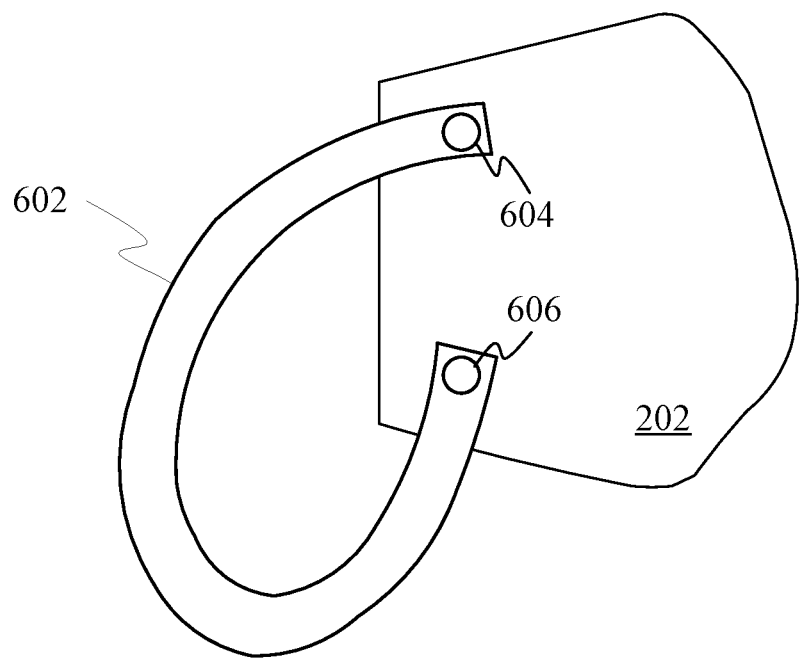

For example, FIG. 6B shows a configuration in which hinge 604 is positioned against one end stop and hinge 606 is positioned against another end stop. In such a configuration, controller 206 of earbud 200 can be configured to emit audio consistent with a right channel, or that of a user's right ear. When compliant member 602 is oriented as shown in FIG. 6C in the opposite direction controller 206 can deliver only a left channel or music consistent with a user's left ear. This configuration would allow earbud 200 to be interchangeable between a left ear and a right ear. In some embodiments, earbud 200 can be configured to enter a power-saving mode when neither of hinges 604 or 606 are positioned at an end stop. Such a configuration would be useful in configurations where at least one of hinges 604 and 606 would necessarily be at an end stop if properly inserted in the ears of a user. Any of these automated features could be enabled or disable by way of a device configured to control operations of earbud 200. Hinges 604 and 606 could also include a spring based biasing member that returns compliant member 602 to the neutral configuration depicted in FIG. 6A. This would prevent the contacts from being actuated while not in use and could also provide a consistent user experience when placing the earbud within the ear of a user.

Figure 7A:
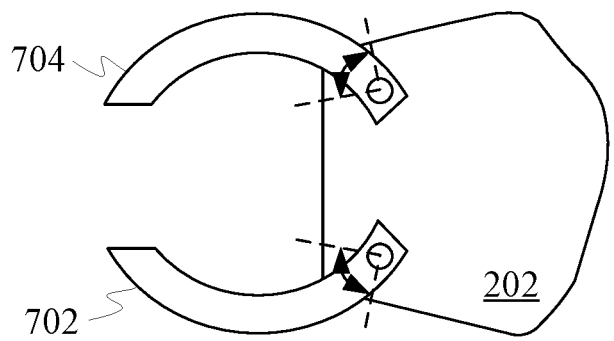
FIGS. 7A-7C show a number of alternate embodiments of the deformable loop depicted in FIGS. 6A-6C.
Figure 7B:
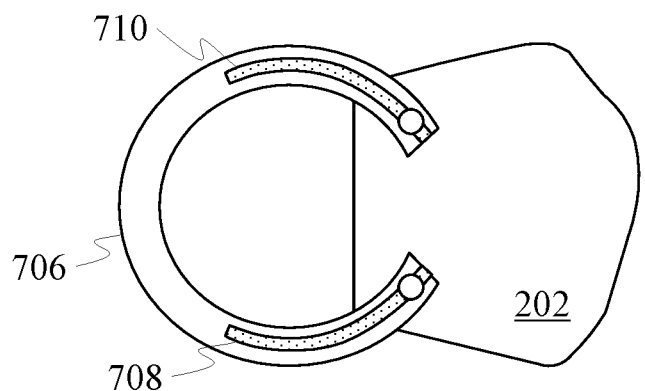
Figure 7C:
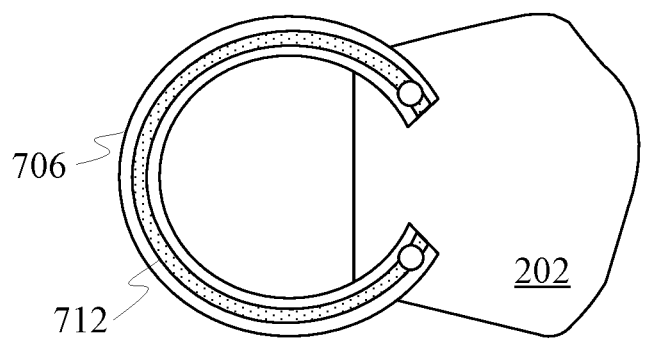

FIGS. 7A-7C show various alternative earbud configuration similar to the configuration depicted in FIGS. 6A-6C. In FIG. 7A a compliant member takes the form of two wings 702 and 704, each wing having one end pivotally coupled with housing 202. In this configuration, wing 702 and wing 704 can act independently of one another while still including the hinge stops discussed with respect to embodiments depicted in FIGS. 6A-6C. FIG. 7B shows an embodiment having a loop 706 of flexible material reinforced by two metal reinforcing members 708 and 710. This configuration can be desirable to increase a rigidity of loop 706, where loop 706 wouldn't otherwise be able to provide a firm enough fit to keep earbud 200 firmly secured within the ear of a user of earbud 200. By leaving a central portion of loop 706 free of reinforcing material a portion of loop 706 that contacts the concha of a user's ear can be substantially softer and provide a more comfortable fit and user experience. FIG. 7C shows a configuration in which reinforcing member 712 takes the form of a continuous length of reinforcing material embedded within loop 706, which can provide a uniform stiffness and resistance for loop 706. A thickness of and material used to construct reinforcing member 712 can be adjusted to achieve a desired amount of resistance in loop 706.

Figure 8A:
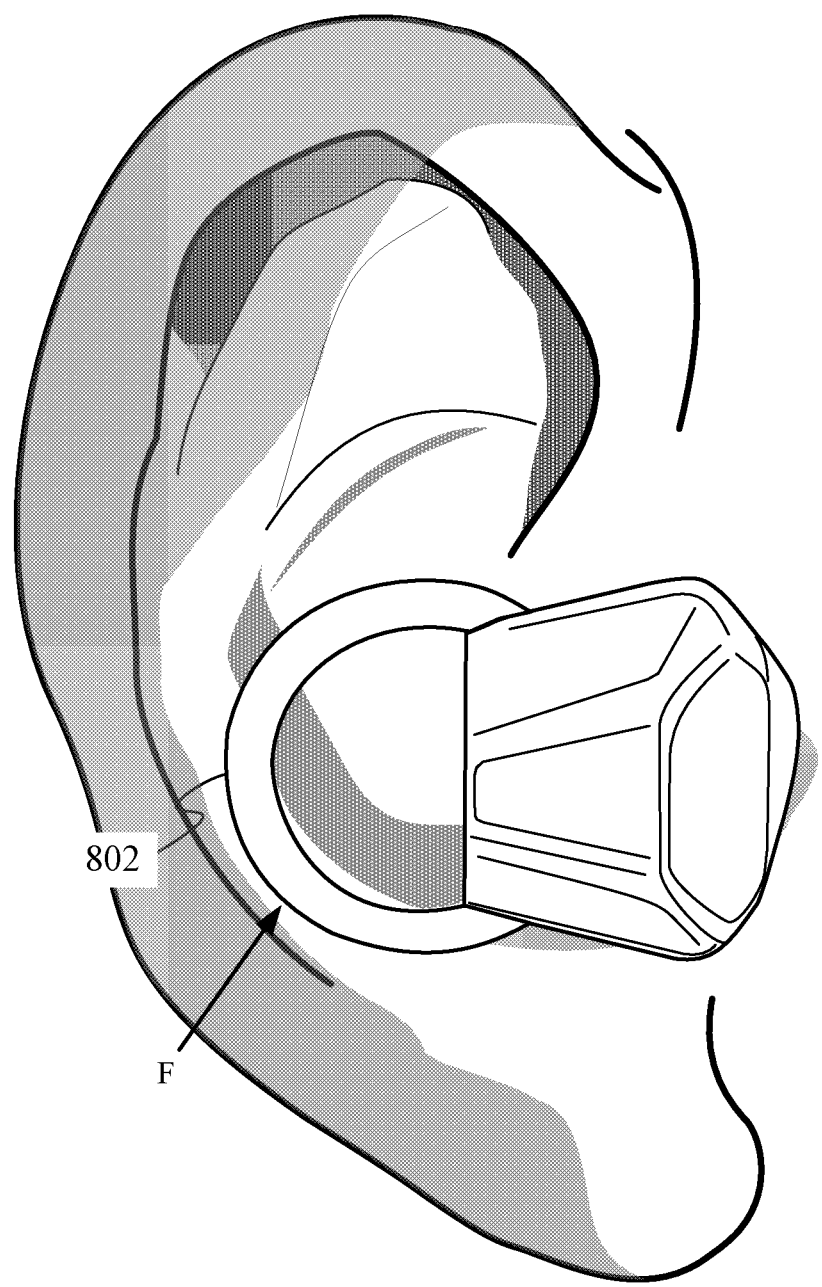
FIGS. 8A-8B show how the deformable loop conforms to the ear of a user of the earbud.
Figure 8B:
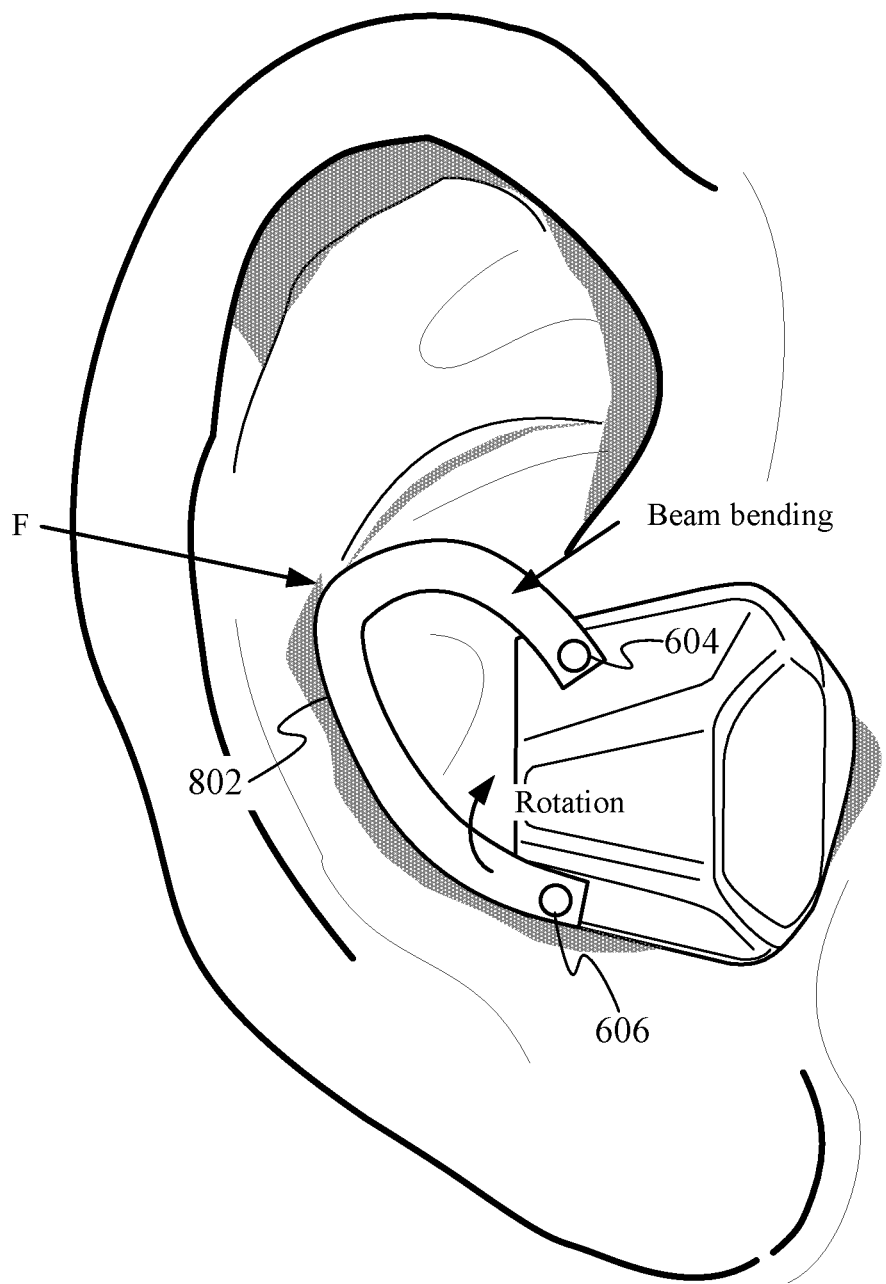

FIG. 8A shows how loop 802 in an undeformed configuration is incompatible with a shape of the ear of a user, and also depicts a direction in which a force F can be exerted upon loop 802 to deform loop 802 for positioning it within the ear of a user. FIG. 8B shows a configuration similar to that depicted in FIG. 6B and illustrates how the natural geometry of the ear causes this type of deformation to occur to loop 802. Because hinge 606 is configured to accommodate rotation of the bottom end of the loop past a horizontal position any force exerted through hinge 606 doesn't tend to push housing 202 out of position but rather ends up exerting a force F with a downward component on housing 202 that tends to keep housing 202 firmly in position while being utilized.

Figure 9:
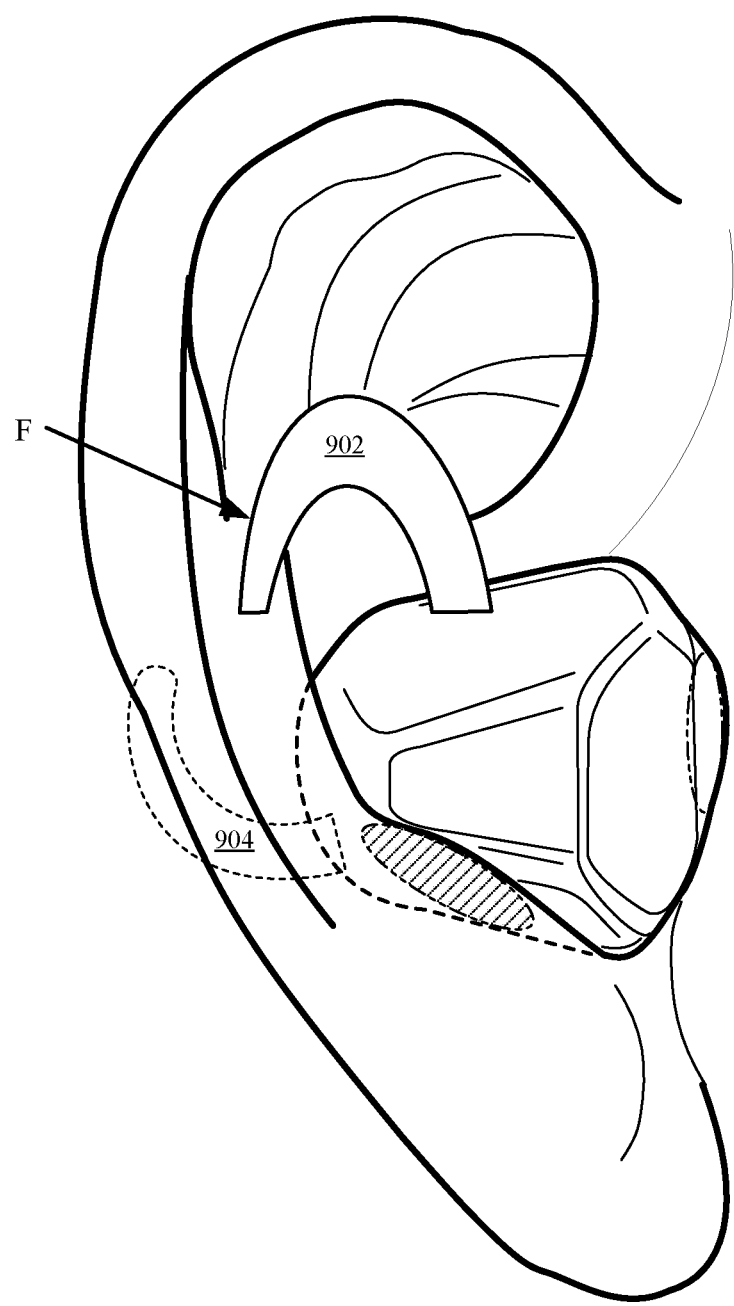
FIG. 9 show an embodiment in which the compliant member takes the form of a single compliant member with one end protruding from the earbud.

FIG. 9 shows a configuration having wings similar to those depicted in FIG. 7A; however, FIG. 9 is laid out to show how it may be desirable to have only an upper wing 902 as a lower wing 904 could interfere and be harder to position within the ear. In a single wing configuration, a user would be able to distinguish which ear to put each earbud in by choosing an earbud that fits within the ear in a way that arranges the wing in an orientation facing the upper portion of the ear of the user. Upper wing 902 can be formed of an elastomeric material and have blunt conformable end that can be positioned comfortably within the ear of a user. A width and resiliency of upper wing 902 can be tuned to provide a desired fit.

Figure 10A:
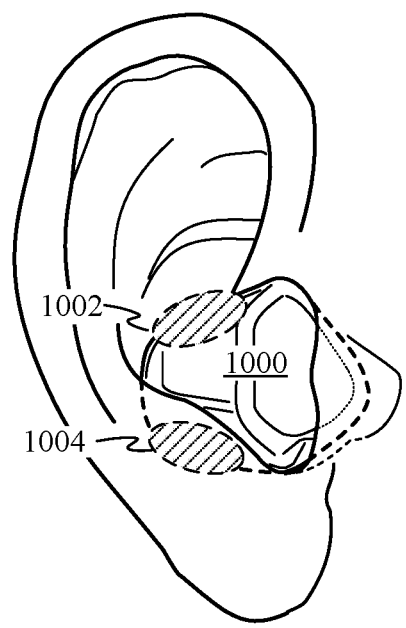
FIGS. 10A-10B show an earbud positioned within the ear of a user with sensors configured to determine an orientation of the earbud.
Figure 10B:
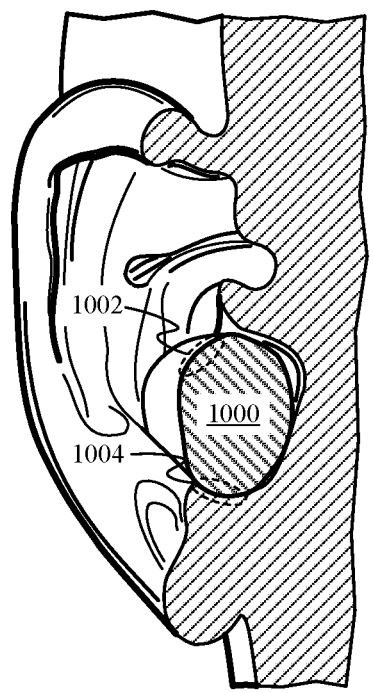

FIGS. 10A-10B show a side view and a partial cross-sectional view respectively of a multi-sensor earbud 1000 disposed within the ear of a user. FIG. 10A points out sensing regions 1002 and 1004 of multi-sensor earbud 1000. When sensors associated with sensing regions 1002 and 1004 are capable of identifying direct contact between an associated sensing region and a surface of the ear, then those sensors can be used to determine an orientation of the multi-sensor earbud 1000 within the ear. Both FIGS. 10A and 10B illustrate why this would be the case since regardless of which ear multi-sensor earbud 1000 is positioned in one of sensing regions 1002 and 1004 is in direct contact with the ear and the other sensing region is not. One type of sensor that can detect contact between a sensing region and the ear is a proximity sensor. The proximity sensor can take the form of an infrared light emitter and receiver. By transmitting infrared light and receiving the infrared light bounced back off the ear, the proximity sensor can determine a distance between the corresponding sensing region and the ear. By measuring a distance between the proximity sensor and the nearest object, a proximity sensor associated with sensing region 1004 could be able to confirm that multi-sensor earbud 1000 is situated in the right ear of a user. Another type of sensor that can accomplish the orientation determination would be a temperature sensor. If multi-sensor earbud 1000 included two temperature sensors, one associated with each sensing region, a controller or processor within multi-sensor earbud 1000 could be configured to compare the two temperature readings and determine from the temperature differential whether: (a) the earbud is inserted in an ear at all; and (b) what the orientation of multi-sensor earbud 1000 is within the ear. In addition to its use as a temperature sensor, a temperature sensor determined to be in direct contact with a user's ear could be used to provide core temperature information, while the second temperature sensor could be configured to provide an ambient temperature In the depicted embodiment, the temperature sensor associated with sensing region 1004 would experience a substantially higher temperature than the temperature associated with sensing region 1002. A capacitive sensor could also be used to detect positive contact between the sensing regions and the ear of the user.

Any of the aforementioned sensor configurations could also be used to identify whether or not the earbud is inserted in the ear of a user at all. A power management utility can be adapted to manage an operational state of multi-sensor earbud 1000 in accordance with that information. Multi-sensor earbud 1000 can include many operational states including, for example, a media playback mode, a standby mode, a disabled mode and a noise cancelling mode. When the power management utility determines multi-sensor earbud 1000 is no longer being worn it can be configured to change the operational state from the playback or noise cancelling mode to the standby or disabled mode. While numerous examples of non-conventional orientation sensors have been discussed it should be appreciated that an inertial orientation sensor can also be used and is contemplated within the scope of this disclosure. As can be appreciated a basic orientation sensor would also be capable of distinguishing between two opposing orientations.

Figure 11:
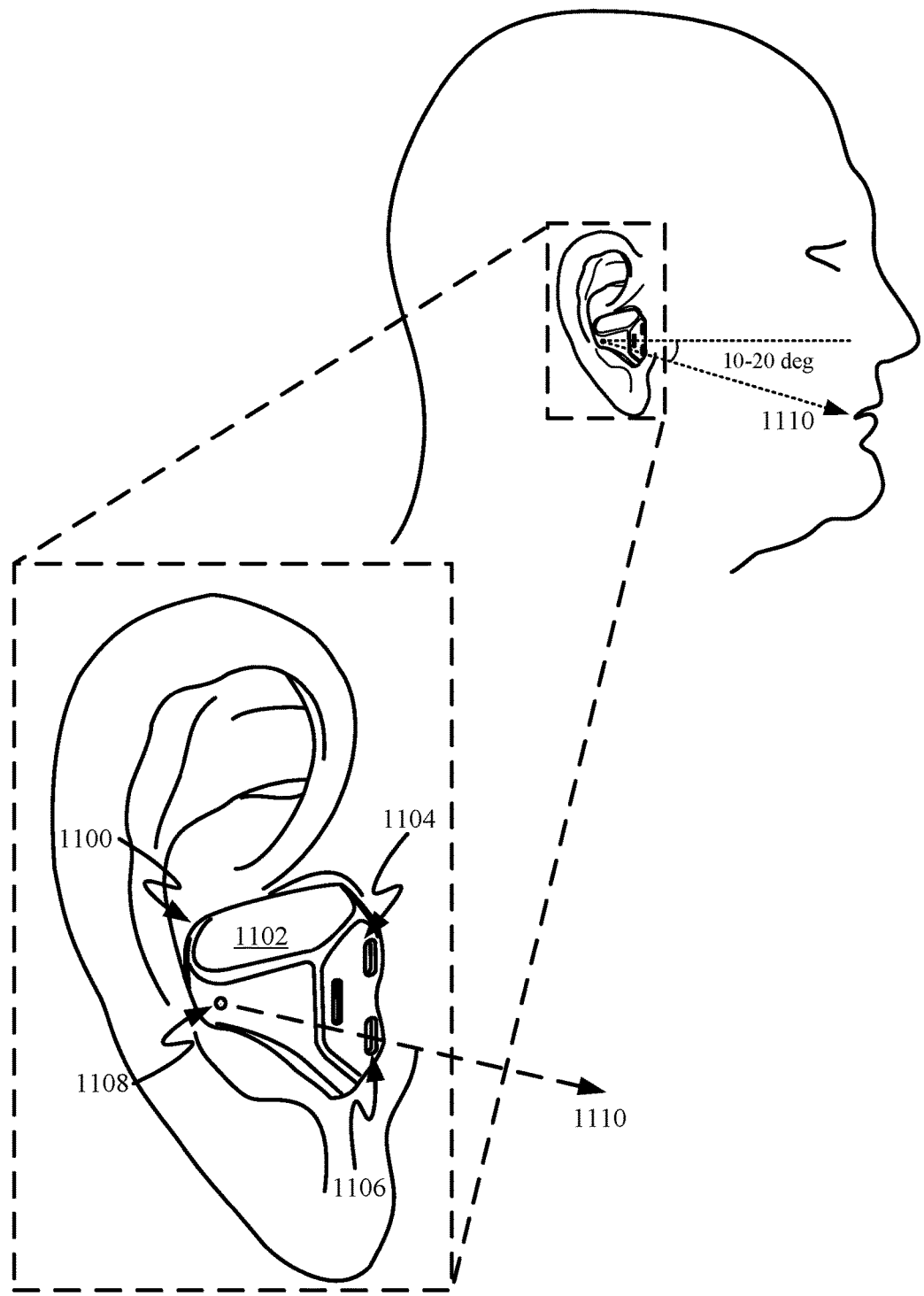
FIG. 11 shows an earbud having a housing that defines multiple openings for receiving audio content at multiple microphones.

FIG. 11 shows an earbud 1100 positioned within an ear of a user. Housing 1102 of earbud 1100 includes numerous microphone openings through which audio signals can propagate to microphones disposed within housing 1102 of earbud 1100. FIG. 11 depicts two front microphone openings 1104 and 1106 and one rear microphone opening 1108, the three openings being arranged in a triangular configuration. These microphone openings can be arranged in a symmetric configuration so that earbud 1100 can operate in a consistent manner regardless of which ear earbud 1100 is positioned in. Microphones positioned within earbud housing 1102 and behind each microphone opening can be configured for many different purposes. In some embodiments, an operational mode of each microphone can be adjusted in accordance with orientation data collected by an orientation sensor of earbud 1100 as described above in relation to FIGS. 10A-10B.

Once an orientation sensor or sensors configured to provide orientation information provide orientation data to a controller within earbud 1100, the controller can compare signals received from both microphones using a spatial filtering process that removes any audio information not arriving within a region 10-20 degrees on either side of a direction 1110 along which microphone openings 1106 and 1108 are both arranged. The spatial filtering can be conducted in many ways, but in one particular embodiment, a time difference of arrival technique can be used, which includes comparing a time at which audio signals are received at a first one of the microphones to a time at which the same audio signals are received at the second microphone to determine a time delay. While time difference of arrival calculations generally require three sampling points to determine a direction of arrival, because microphone openings 1106 and 1108 are aligned with a direction of the desired sampling source only two sampling sources are required in this type of configuration.

In some embodiments, all content arriving first at microphone opening 1108 can be disregarded while all content arriving at microphone opening 1106 first could be included and processed. This would allow only audio content arriving from a direction in which the user was facing to be recorded. In some embodiments, a delay associated with an audio signal traveling directly along direction 1110 can be known. To allow for an amount of variation in a direction of arrival of speech from the user to be accommodated any delay within 20% of the known delay period can be processed. In still other embodiments, the microphone array can be configured to collect only the top percentage of audio having the longest delay period where audio arrives first at microphone opening 1106. This configuration could be desirable when a user wished to record ambient audio signals when not actively speaking. For example, the microphone array could switch between modes where only the user is being recorded to a mode where ambient audio is collected after a predetermined period of time passes with no speech being detected from the user. In some embodiments, any errors created by variation between a direction from which speech reaches the microphone array and an orientation of microphone openings 1106 and 1108 can be ameliorated by calibration software configured to adjust a collection window in accordance with the variations. In some embodiments, the calibration software can be hosted upon a device such as portable media device 100.

In some embodiments, unused microphone opening 1104 can be configured to carry out other functions. For example, a controller within earbud 1100 can be configured to process audio content received by a microphone positioned behind microphone opening 1104 to provide noise cancellation capabilities to earbud 1100. In some embodiments, the noise cancelling provided by earbud 1100 can be setup to provide selective noise cancelling which allows any audio received within the 10-20 degree window to be allowed through, while in other embodiments, substantially all audio can be screened out. In this way, during a conversation a person's own voice wouldn't prevent the speaker from being able to hear other speakers attempting to enter or participate in a conversation. In some embodiments, a microphone associated with microphone opening 1104 can be used in conjunction with other microphones to provide more detailed information upon a direction from which an audio signal originates. Alternatively, a microphone associated with microphone opening 1104 can just be disabled or turned off until orientation data is provided indicating a change in orientation of earbud 1100. In some embodiments, a change in orientation data indicating earbud 1100 had been placed in the other ear of the user would result in functions carried out by microphones associated with microphone openings 1104 and 1106 being swapped. Alternatively, housing 1102 can only include two microphone openings, for example, just openings 1106 and 1108. In such an embodiment, if a user was utilizing one earbud 1100 in each ear, only one of the earbuds would have microphone openings directed towards a mouth of a user. Orientation data or audio sampling processes could be used to determine which earbud had microphone openings aligned with the mouth of the user.

In addition to swapping functionality of microphones associated with microphone openings 1104 and 1106, when a user is actively utilizing a set of earbuds 1100, the microphones can periodically sample audio from both earbuds at which point a processor either within one or both of earbuds 1100 or a paired device along the lines of portable media device 100 can compare both samples and direct the earbud with better quality to be activated while leaving the other earbud microphones in a standby or periodic sampling mode. Furthermore, since operation of the microphones can consume battery power, microphones within an earbud can be activated when that earbud has a substantially greater battery charge than the other earbud.

Figure 12:
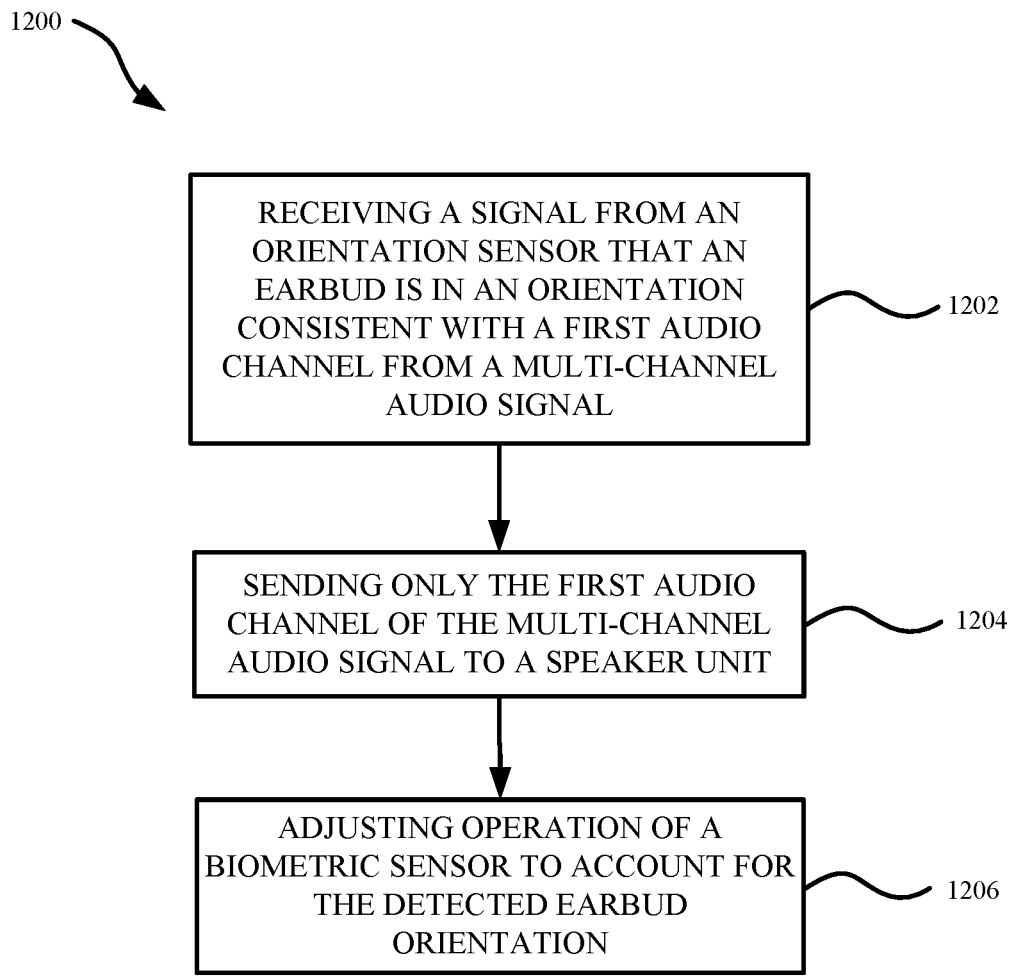
FIG. 12 shows a flow chart depicting a process for determining an orientation of an earbud within the ear of a user.

FIG. 12 shows a flow chart illustrating a method for determining an orientation of an earbud within the ear of a user. In a first block 1202, a signal is received at a processor or controller of the earbud from an orientation sensor of the earbud indicating an orientation of the earbud is consistent with a first audio channel of a multi-channel audio signal. The orientation sensor can take many forms including but not limited to a conventional inertial sensor, a temperature sensor, a proximity sensor, a capacitive sensor or the like. In a second block 1204, the processor sends only the first audio signal of the multi-channel audio signal to a speaker unit. The first audio channel can represent one of a left or right channel of the multi-channel audio signal when the multi-channel audio signal is a stereo audio signal. Alternatively, orientation sensor information can be used to continuously update channel information. For example, if it is determined that only a single earbud is being used, the channels can be combined into a single channel or a combined channel creating virtual left and right channels within a single earbud can be carried out. In this way, a more consistent audio experience can be achieved by preventing content normally routed through the removed earbud from being missed. In block 1206, an operating state of a sensor of the earbud is adjusted in accordance with orientation sensor data from the orientation sensor. In some embodiments, a biometric sensor can be arranged to focus its readings on a portion of the body most likely to provide high quality biometric parameters. For example, light emitted from a PPG sensor can be angled to focus on a portion of the tragus likely to be well-profused with blood. In another embodiment, orientation sensor data can be used in determining which sensors should be activated and/or deactivated. In some embodiments, roles or operational states for an array of sensors can be assigned based upon the orientation data. In these ways, orientation information can be utilized to optimize a user experience of one or more earbuds.

The various aspects, embodiments, implementations or features of the described embodiments can be used separately or in any combination. Various aspects of the described embodiments can be implemented by software, hardware or a combination of hardware and software. The described embodiments can also be embodied as computer readable code on a computer readable medium for controlling manufacturing operations or as computer readable code on a computer readable medium for controlling a manufacturing line. The computer readable medium is any data storage device that can store data which can thereafter be read by a computer system. Examples of the computer readable medium include read-only memory, random-access memory, CD-ROMs, HDDs, DVDs, magnetic tape, and optical data storage devices. The computer readable medium can also be distributed over network-coupled computer systems so that the computer readable code is stored and executed in a distributed fashion.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It will be apparent to one of ordinary skill in the art that many modifications and variations are possible in view of the above teachings.

What is claimed is:

1. An earbud, comprising:
   an earbud housing defining an opening;
   a speaker disposed within the earbud housing and oriented so that audio emitted by the speaker exits the earbud housing through the opening; and
   a compliant member coupled to the earbud housing and comprising:
      a loop of flexible material,
      a first reinforcing member extending along a length of a first portion of the loop;
      a second reinforcing member extending along a length of a second portion of the loop, and
      a third portion of the loop disposed between the first and second portions and free of reinforcing material such that the third portion of the loop is less rigid than the first and second portions of the loop.

2. The earbud as recited in claim 1, wherein the first and second reinforcing members are the same length.

3. The earbud as recited in claim 1, wherein the flexible material is an elastomeric material that is less rigid than the first and second reinforcing members.

4. The earbud as recited in claim 3, wherein the first and second reinforcing members comprise spring steel.

5. The earbud as recited in claim 1, wherein the flexible material at least partially encloses the first reinforcing member and the second reinforcing member.

6. The earbud as recited in claim 5, wherein the first portion of the loop is positioned adjacent to the earbud housing and the second portion of the loop is positioned adjacent to the earbud housing.

7. The earbud as recited in claim 1, wherein the compliant member is pivotally coupled to the earbud housing by a hinge.

8. An earbud, comprising:
   an earbud housing defining an opening;
   a speaker disposed within the earbud housing and oriented so that audio emitted by the speaker exits the earbud housing through the opening; and
   a compliant member coupled to the earbud housing, the compliant member comprising:
      a loop formed from a flexible material, the loop comprising a first portion at least partially enclosing a first interior volume, a second portion at least partially enclosing a second interior volume and a third portion disposed between the first and second portions;

a first reinforcing member disposed within the first interior volume and extending along a length of the first portion; and a second reinforcing member disposed within the second interior volume and extending along a length of the second portion such that the third portion of the loop is less rigid than the first and second portions of the loop.

9. The earbud as recited in claim 8, wherein the flexible material is elastomeric.

10. The earbud as recited in claim 8, wherein the first and second reinforcing members are positioned on opposing ends of the loop.

11. The earbud as recited in claim 8, wherein the first portion is adjacent to a first location on the earbud housing and the second portion is adjacent to a second location on the earbud housing offset from the first location.

12. The earbud as recited in claim 8, wherein the compliant member is positioned on a first side of the earbud housing and the opening defined by the earbud housing is positioned on a second side of the earbud housing.

13. The earbud as recited in claim 8, wherein the first portion of the loop is closer to the earbud housing than the third portion of the loop.

14. An earbud, comprising:

an earbud housing;

a speaker disposed within the earbud housing and oriented so that audio emitted by the speaker exits the earbud housing through an opening; and a compliant member coupled to the earbud housing and comprising a loop of flexible material, and a reinforcing member extending along a length of a first portion of the loop, the first portion of the loop having a higher rigidity than a second portion of the loop.

15. The earbud as recited in claim 14, wherein a first end of the complaint member protrudes from a first location on the earbud housing and a second end of the compliant member protrudes from a second location on the earbud housing.

16. The earbud as recited in claim 14, wherein the reinforcing member is a first reinforcing member and the compliant member further comprises a second reinforcing member extending along a length of a third portion of the loop.

17. The earbud as recited in claim 16, wherein the second portion of the loop is positioned between the first and third portions of the loop and the second portion of the loop is positioned farther from the earbud housing than both the first and third portions of the loop.

18. The earbud as recited in claim 16, wherein the compliant member comprises a length of flexible material that encloses both the first and second reinforcing members.

19. The earbud as recited in claim 14, wherein the compliant member is configured to keep the earbud housing secured within an ear of a user.

20. The earbud as recited in claim 14, wherein the earbud housing comprises a protrusion, a distal end of the protrusion defining the opening.

* * * * *